US010149476B2

(12) United States Patent
Pennell

(10) Patent No.: US 10,149,476 B2
(45) Date of Patent: Dec. 11, 2018

(54) PESTICIDAL PLANT EXTRACT CONTAINING LOLINE DERIVATIVES

(71) Applicant: GRASSLANZ TECHNOLOGY LTD, Palmerston North (NZ)

(72) Inventor: Christopher Gerald Lee Pennell, Rangiora (NZ)

(73) Assignee: Grasslanz Technology Ltd, Palmerston North (NZ)

(*) Notice: Subject to any disclaimer, the term of this patent is extended or adjusted under 35 U.S.C. 154(b) by 543 days.

(21) Appl. No.: 14/578,153

(22) Filed: Dec. 19, 2014

(65) Prior Publication Data

US 2015/0106976 A1    Apr. 16, 2015

Related U.S. Application Data

(62) Division of application No. 12/531,481, filed as application No. PCT/NZ2008/000052 on Mar. 12, 2008, now Pat. No. 9,375,011.

(30) Foreign Application Priority Data

Mar. 15, 2007  (NZ) .................................. 553892

(51) Int. Cl.
    A01N 43/90         (2006.01)
(52) U.S. Cl.
    CPC ....................... A01N 43/90 (2013.01)
(58) Field of Classification Search
    None
    See application file for complete search history.

(56) References Cited

U.S. PATENT DOCUMENTS

| | | |
|---|---|---|
| 5,185,028 A | 2/1993 | Powell et al. |
| 5,492,902 A | 2/1996 | Belofsky et al. |
| 5,720,972 A | 2/1998 | Munday |
| 6,072,107 A | 6/2000 | Latch et al. |
| 6,111,170 A | 8/2000 | Latch et al. |
| 6,372,239 B1 | 4/2002 | Wu et al. |
| 6,416,782 B1 | 7/2002 | Maas |
| 7,037,879 B2 | 5/2006 | Imada et al. |
| 7,052,708 B2 | 5/2006 | O'Leary |
| 7,642,424 B2 | 1/2010 | Van Hanja et al. |
| 7,976,857 B2 | 7/2011 | Tapper et al. |
| 8,101,400 B2 | 1/2012 | Rolston et al. |
| 2004/0141955 A1 | 7/2004 | Strobel et al. |
| 2005/0150024 A1 | 7/2005 | West et al. |
| 2005/0181074 A1 | 8/2005 | Watson et al. |
| 2006/0121593 A1 | 6/2006 | Christensen et al. |

FOREIGN PATENT DOCUMENTS

| | | |
|---|---|---|
| GB | 2333451 | 7/1999 |
| JP | 2003192516 A | 7/2003 |
| NZ | 228233 | 9/1990 |
| NZ | 241391 | 4/1994 |
| NZ | 278977 | 3/1997 |
| NZ | 233083 | 7/2001 |
| RU | 2201678 C2 | 4/2003 |
| WO | WO 92/005776 | 4/1992 |
| WO | WO97/037540 | 10/1997 |
| WO | WO00/065912 | 11/2000 |
| WO | WO01/078510 | 10/2001 |
| WO | WO 01/087273 | 11/2001 |
| WO | WO 2002/13616 | 2/2002 |
| WO | WO 02/089763 | 11/2002 |
| WO | WO 2004/106487 | 12/2004 |

OTHER PUBLICATIONS

TePaske et al. J. Agric. Food Chem. WSS, 41, 2299-2303.*
Bacon et al. "3. Abiotic Stress Tolerance of endophyte-infected grasses: 3.1. Drought Stress Tolerance". from Microbial Endophytes. (2000). 1 page.*
Young et al. Applied and Environmental Microbiology, Apr. 2009, p. 2200-2211.*
Linde-Laursen et al. Hereditas 116 (1992) pp. 111-116.*
Dougherty, et al., "Mortality of horn fly (Diptera: Muscidae) larvae in bovine dung supplemented with loline alkaloids from tall fescue" J. Medical Entomol. (1998) 35(5): 798-803.
Riedell, et al., "Naturally-occurring and synthetic loline alkaloid derivatives: Insect feeding behavior modification and toxicity" J. Entomol. Sci. (1991) 26(1): 122-129.
Rowan, et al., "Isolation of feeding deterrents against Argentine stem weevil from ryegrass infected with the endophyte Acremonium loliae" J. Chem. Ecol. (1986) 12(3): 647-658.
Yates, et al., "Assay of tall fescue seed extracts, fractions, and alkaloids using the large milkweed bug" J. Agric. Food Chem. (1989) 37: 354-357.
International Search Report, dated May 22, 2008, issued in International Application No. PCT/NZ2008/000052.
Cloyd, Raymond, "Systemic, Local Systemic, or Translaminar Insecticides: What's the Difference?" Home, Yard & Garden Pest Newsletter, University of Illinois Extension, Nov. 27, 2002, available at http://hyg.ipm.illinois.edu/pastpest/200220e.html.
Justus, et al., "Levels and Tissue Distribution of Loline Alkaloids in Endophyte-Infected *Festuca pratensis*," Phytochemistry, vol. 44, No. 1., pp. 51-57, 1997.
Wilkinson et al. MPMI vol. 13, No. 10, 2000, pp. 1027-1033.
"Insect Treatment", Internet Archive Date: Feb. 2, 1999 [Retrieved from the Internet on: Jan. 23, 2014]. Retrieved from: <URL:https://web.archive.org/web/19990202145425/http://www.ghorganics.com/page14.html>.

(Continued)

Primary Examiner — Amy L Clark
(74) Attorney, Agent, or Firm — Knobbe, Martens, Olson & Bear, LLP

(57) ABSTRACT

This invention relates to a pesticidal compositions containing at least one pyrrolizidine alkaloid compound derived from a plant and endophyte combination, and applying the pesticidal compositions to another plan without pesticidal protection, where upon application of the composition, the plant confers pest protection. The pyrrolizidine alkaloid compound is of Formula (I) wherein: R=H or $CH_3$ and R'=H, $CH_3$, CHO, $COCH_3$.

8 Claims, 4 Drawing Sheets

(56) References Cited

OTHER PUBLICATIONS

Figure 1:
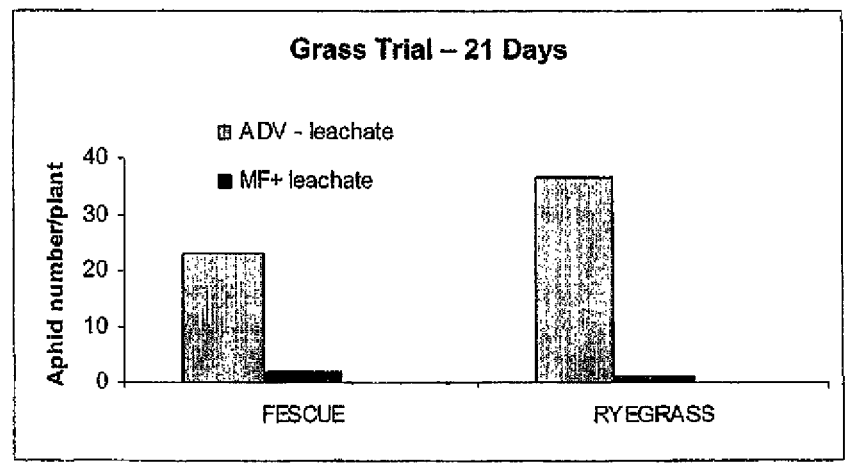
Figure 2:
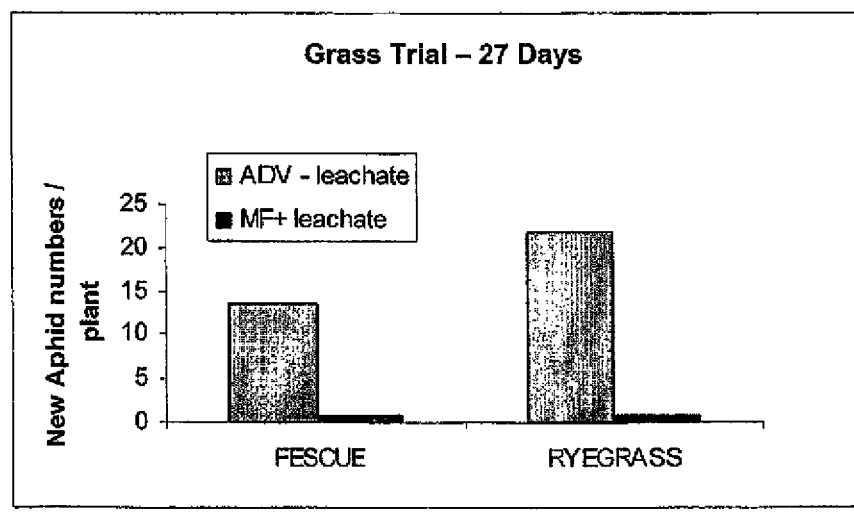
Figure 3:
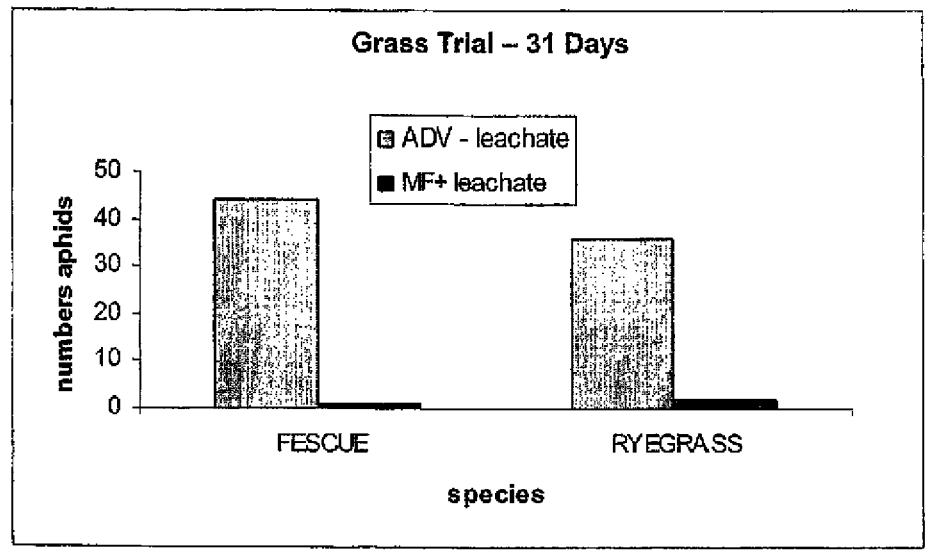

Wiedenfeld et al. Phytochemistry 57 (2001) 1269-1271.
Johnson et al. Applied and Environmental Microbiology, Mar. 1985, p. 568-571.
"The World's Healthiest Foods", Retrieved from the Internet on: Jan. 23, 2014. Retrieved from: URL: http://www.whfoods.com/genpage.php?tname=george&dbid=206.
Australian Government Analytical Laboratories (AGAL) accession No. NM03/35819 (*Neotyphodium lolii* AR37), dated May 23, 2003.
Australian Government Analytical Laboratories (AGAL) accession No. NM03/35820 (*Neotyphodium lolii* AR40), dated May 23, 2003.
Ball, et al. 1997. Ergopeptine alkaloids and *Neotyphodium lolii*-mediated resistance in perennial ryegrass against *Heteronychus arator* (Coleoptera: Scarabaeidae). *Journal of Economic Entomology*, 90(5):1382-1391.
Ball, et al., "Effect of Selected Isolates of Acremonium Endophytes on Adult Black Beetle (*Heteronychus arator*) Feeding" *Proc 47th N.Z. Plant Protection Conf* (1994): 227-231.
Barker, et al. 1993. Effect of water deficit on alkaloid concentrations in perennial ryegrass endophyte associations. In *Proceedings of the Second International Symposium on Acremonium/Grass Interactions*. Eds. Hume, D. E.; Latch, G. C. M.; Easton, H. S. AgResearch, New Zealand, pp. 67-71.
Belofsky, et al. 1995. Antiinsectan alkaloids: Shearinines A-C and a new paxilline derivative from the ascostromata of *Eupenicillium shearii*. *Tetrahedron*, 51(14):3959-3968.
Blackwell, et al., "Efficacy of aircraft landing lights in stimulating avoidance behavior in birds", *J. of Wildlife Management*, (Jul. 2004) 68(3): 725-732.
Blank, et al. 1992. Soilborne seedling diseases of tall fescue: Influence of the endophyte, *Acremonium coenophialum*. *Phytopathology*, 82(10):1089.
Bluett et al., "Effects of a novel ryegrass endophyte on pasture production, dairy cow milk production, and calf liveweight gain", *Australian Journal of Experimental Agriculture* (2005) 45(1):11-19.
Bouton, et al. 2002. Reinfection of tall fescue cultivars with non-ergot alkaloid-producing endophytes. *Agronomy Journal*, 94(3):567-574.
Bultman, et al. 2003. Isolate-dependent impacts of fungal endophytes in a multitrophic interaction. *Oikos*, 102:491-496.
Bush et al., "Chemistry, occurrence and biological effects of saturated pyrrolizidine alkaloids associated with endophyte-grass interactions", Agriculture, Ecosystems and Environment, 44 (1993) 81-102.
Christensen, et al., "Occurrence of the fungal endophyte *Neotyphodium coenophialum* in leaf blades of tall fescue and imp0lications for stock health" *NZ J of Ag Res* (1998) 41: 595-602.
Clay, Keith, "Symbiosis and the Regulation of Communities" *Amer. Zool.*, (2001) 41: 810-824.
Conover, et al., "Feeding Preferences and Changes in Mass of Canada Geese Grazing Endophyte-Infected Tall Fescue" *The Condor*, (1996) 98: 859-862.
Crush, et al. 2004. Effect of different *Neotyphodium* endophytes on root distribution of a perennial ryegrass (*Lolium perenne* L.) cultivar. *New Zealand Journal of Agricultural Research*, 47:345-349.
de Jesus, et al. 1984. Structure elucidation of the janthitrems, novel tremorgenic mycotoxins from *Penicillium janthinellum*. *Journal of the Chemical Society, Perkin Transactions I*, 4:697-701.
Dolbeer, et al., "Anthraquinone Formulation (Flight Control) Shows Promise as Avian Feeding Repellent" *J. of Wildlife Management*, (1998) 62(4): 1558-1564.
Dolbeer, et al., "Ranking the hazard level of wildlife species to aviation", *Wildlife Society Bulletin*, (2000) 28(2): 372-378.
Durham, et al., "Effect of endophyte consumption on food intake, growth and reproduction in prairie voles", *Canadian J. of Zoology*, (May 1998) 76: 960-969.
Elbersen, et al. 1996. Growth and water relations of field-grown tall fescue as influenced by drought and endophyte. *Grass and Forage Science*, 51:333-342.

European Search Report dated Sep. 22, 2009, issued in European Application No. 06784009.0.
Fletcher, et al. 1999. The impact of endophyte on the health and productivity of sheep grazing ryegrass-based pastures. In *Ryegrass Endophyte: An Essential New Zealand Symbiosis*. Grassland Research and Practice Series No. 7, pp. 11-17.
Fletcher, et al. 2000. Using endophytes for pasture improvement in New Zealand. In Proceedings of The Grassland Conference 2000, 4th International Neotyphodium/Grass Interactions Symposium. Eds. Paul, V. H.; Dapprich, P. D., Universtät, Paderborn, pp. 149-162.
Fletcher, L. R. 1999. "Non-toxic" endophytes in ryegrass and their effect on livestock health and production. In *Ryegrass Endophyte: An Essential New Zealand Symbiosis*. Grassland Research and Practice Series No. 7, pp. 133-139.
Gallagher, et al. 1980. The janthitrems: Fluorescent tremorgenic toxins produced by *Penicillium janthinellum* isolates from ryegrass pastures. *Applied and Environmental Microbiology*, 39(1):272-273.
Gosser, et al., *Managing Problems Caused by Urban Canada Geese*, Berryman Institute Publication 13, (1997) Utah State University, Logan.
Griffiths, et al. 1999. Non-radioactive AFLP fingerprinting for detection of genetic variation in *Epichloë/Neotyphodium* endophytes. Proceedings of the 11th Australian Plant Breeding Conference, Adelaide, vol. 2, pp. 212-213.
Hill et al., "Endophyte viability in seedling tall fescue treated with fungicides", *Crop Science* (2000) 40(5): 1490-1491.
International Search Result and Written Opinion dated Dec. 5, 2006 in PCT/NZ2006/000202.
Jensen et al. "Variation in Genetic Markers and Ergovaline Production in Endophyte (*Neotyphodium*)—Infected Fescue Species Collected in Italy, Spain and Denmark." Crop Sci. 47:139-147 (2007).
Latch, et al. 1985. Artificial infection of grasses with endophytes. *Annals of Applied Biology*, 107:17-24.
Leuchtmann, A. 1997. Ecological diversity in *Neotyphodium*-infected grasses as influenced by host and fungus characteristics. In *Neotyphodium/Grass Interactions*, Eds. Bacon, C. W.; Hill, N. S. Plenum Press, New York, pp. 93-108.
Leuchtmann, et al., "Different Levels of Protective Alkaloids in Grasses with Stroma-Forming and Seed-Tranmitted *Epichloë/Neotyphodium* Endophytes" *J. Chem. Ecology* (2000) 26(4): 1025-1036.
Madej, et al., "Avian seed preference and weight loss experiments: the effect of fungal endophyte-infected tall fescue seeds" *Oecologia*, (1991) 88: 296-302.
Meriaux et al., "Effect of fungicides and heat treatment on seed germination of endophyte infected perennial ryegrass", Proceedings of the 19th General Meeting of the European Grassland Federation, La Rochelle, France, May 27-30, 2002; *Grassland Science in Europe* 7: 536-537.
Moon, et al. 1999. Identification of Epichloë endophytes in planta by a microsatellite-based PCR fingerprinting assay with automated analysis. *Applied and Environmental Microbiology*, 65(3):1268-1279.
Park et al., "Isolation and characterization of *Burkholderia cepacia* EP215, An Endophytic Bacterium Showing a Potent Antifungal Activity Against *Colletrotrichum species*", *Korean J. of Microbiology and Biotechnology* (2005) 33(1): 16-23. (Abstract Only).
Penn, et al. 1993. Janthitrems B and C, two principal indolediterpenoids produced by *Penicillium janthinellum*. *Phytochemistry*, 32(6):1431-1434.
Petroski et al., "Isolation, Semi-Synthesis, and NMR Spectral Studies of Loline Alkaloids", Journal of Natural Products, vol. 52, No. 4, pp. 810-817, Jul.-Aug. 1989.
Petroski et al., "Preparative Separation of Complex Alkaloid Mixture by High-Speed Countercurrent Chromatography", ACS Symposium Series 449, Naturally Occurring Pest Bioregulators, American Chemical Society, 1991.
Popay et al. "Cultivar and Endophyte Effects on a Root Aphid, *Aploneura lentisci*, in Perennial Ryegrass." New Zealand Patent Protection. 60:223-227 (2007).

(56) References Cited

OTHER PUBLICATIONS

Popay, et al. 1995. Resistance to Argentine stem weevil in perennial ryegrass infected with endophytes producing different alkaloids. *Proc. 48th N.Z. Plant Protection Conf.*, pp. 229-236.

Prestidge, et al. 1985. Lolitrem B—A stem weevil toxin isolated from *Acremonium*-infected ryegrass. Proceedings 38th New Zealand Weed and Pest Control Conference, pp. 38-40.

Rolston et al., "Tolerance of AR1 Neotyphodium endophyte to fungicides used in perennial ryegrass seed production", *NZ Plant Protection* (Aug. 2002) 55: 322-326.

Rolston, M.P. and Agee, C. 2007. Delivering Quality Seed to Specification—the USA and NZ Novel Endophyte Experience. Proceedings of the 6th International Symposium on Fungal Endophytes of Grasses. Grasslands Research and Practice Series No. 13: 229-231.

Rowan, et al. 1986. Peramine, a novel insect feeding deterrent from ryegrass infected with the endophyte *Acremonium loliae*. *Journal of the Chemical Society. Chem. Commun.*, pp. 935-936.

Rowan, et al. 1990. Effect of fungal metabolite peramine and analogs on feeding and development of Argentine stem weevil (*Listronotus bonariensis*). *Journal of Chemical Ecology*, 16(5):1683-1695.

Rowan, et al. 1994. Utilization of endophyte-infected perennial ryegrasses for increased insect resistance. In *Biotechnology of Endophyte Fungi in Grasses*. Eds. Bacon, C. W., White, J. CRC Press, pp. 169-183.

Saiga et al., "Endophyte removal by fungicides from ramets of perennial ryegrass and tall fescue", *Grassland Science* (2003) 48(6): 504-509.

Siegel et al., "A fungal endophyte of tall fescue: evaluation of control methods", *Phytopathology* (1984) 74(8): 937-941.

Siegel, et al., "Fungal Endophyte-Infected Grasses: Alkaloid Accumulation and Aphid Response" *J. Chem. Ecology* (1990) 16(12): 3301-3315.

Spiering et al. "Simplified Extraction of Ergovaline and Peramine for Analysis of Tissue Distribution in Endophyte-Infected Grass Tillers." Journal of Agriculture and Food Chemistry. 50:5856-5862 (2002).

Stuedemann, et al. 1988. Fescue endophyte: History and impact on animal agriculture. *Journal of Production Agriculture*, 1(1):39-44.

Sutherland et al. "Allelopathic effects of endophyte-infected perennial ryegrass extracts on white clover seedings." New Zealand Journal of Agricultural Research. 42:19-26 (1999).

Tapper, et al. 1999. Selection against toxin production in endophyte-infected perennial ryegrass. In *Ryegrass Endophyte: An Essential New Zealand Symbiosis*. Grassland Research and Practice Series No. 7, pp. 107-111.

Timper et al., "Response of *Pratylenchus* spp. In tall fescue infected with different strains of the fungal endophyte *Neotyphoidum coenophialum*" *Nematology* (2005) 7(1): 105-110.

van Zijll de Jong, et al, "Development and characterization of EST-derived simple sequence repeat (SSR) markers of pasture grass endophytes" *Genome* (2003) 46: 277-290.

Wang et al., "Permeabilization of Metabolites from Biologically Viable Soybeans (Glycine max)", Biotechnol. Prog. 2001, 17, 424-430.

Wilkins, et al. 1992. Structure elucidation of janthitrem B, a tremorgenic metabolite of *Penicillium janthinellum*, and relative configuration of the A and B rings of janthitrems B, E, and F. *Journal of Agricultural and Food Chemistry*, 40(8):1307-1309.

Yates et al., "Analysis of Loline Alkaloids in Endophyte-Infected Tall Fescue by Capillary Gas Chromatography", J. Agric. Food Chem., 1990, 38, 182-185.

* cited by examiner

PESTICIDAL PLANT EXTRACT CONTAINING LOLINE DERIVATIVES

STATEMENT OF CORRESPONDING APPLICATIONS

This application is a continuation of U.S. patent application Ser. No. 12/531,481, filed May 27, 2010, which is a U.S. National Phase of International Application No. PCT/NZ2008/000052, filed Mar. 12, 2008, designating the U.S. and published on Sep. 18, 2008 as WO 2008/111861, which claims priority to New Zealand Patent Application No. 553892, filed Mar. 15, 2007, the entire contents of each of which are incorporated herein by reference in their entirety.

TECHNICAL FIELD

The invention relates to alkaloid based pesticidal composition. More specifically the invention relates to a product and methods of providing plants with improved pest protection using naturally produced pyrrolizidine alkaloids.

BACKGROUND ART

Pesticides are useful in protecting plants from attack by various pests including insects. A disadvantage of many pesticides currently marketed are the (perceived or otherwise) issues associated with chemicals and environmental concerns. Another problem is that the chemicals require special handling and may be poisonous or harmful to the person applying the chemical. Ideally, pesticides would be common-place, have no or minimal environmental effects and utilise protection mechanisms already present in nature referred to herein as 'naturally' produced.

Alkaloids, including pyrrolizidine alkaloids, are produced by endophytes as a fungal metabolite when in symbiotic relationships with plant species including grasses. Such endophytes are valued in grasses due to the pest protection the alkaloids produced from the endophytes provide. In effect, the endophyte provides the plant with a natural built in pest protection.

Typically, transferring resistance to another plant e.g. an alternative grass cultivar, has been carried out by infecting the plant with the endophyte. Examples of this process are described in other patents including those pursued by the applicant. A further example is U.S. Pat. No. 7,037,879 which teaches of a method of conferring pest resistance to plants of Poaceae by adding an isolated endophytic bacterium to the Poaceae plant. No teaching is made other than to transfer an endophyte similar to existing methods of transferring endophytic properties amongst grass cultivars. Inoculation may not always be easy or even possible between different plants. In addition, the pesticidal properties desired may not also transfer to other plants where inoculation is successful. It should also be appreciated that an inoculation step requires careful, slow and comparatively expensive techniques.

U.S. Pat. No. 6,372,239 teaches of a composition containing a 'cocktail' of plant alkaloids used as an insecticide. Alkaloids described include anabasine along with a wide variety of other alkaloids from a variety of plants. There is no teaching regarding the alkaloids being endophyte metabolites or the alkaloids being loline type compounds. The formulations described also utilise strong polar solvents with a preferred solvent being mineral turpentine. Such solvents are undesirable due to their cost and environmental impacts.

U.S. Pat. No. 5,185,028 teaches of synthetically produced N-substituted loline derivative compounds and their use as a pesticide in spraying applications. The specification teaches away from use of naturally derived alkaloid compounds claiming synthetic compounds with a differing $C_4$ to $C_{20}$ $R_1$ group to naturally occurring pyrrolizidine alkaloid compounds. The specification also teaches that the synthetic loline derivative be mixed with strong solvents to form a liquid which, as noted above is not desirable. Further, the specification teaches that the solution should be applied at the locus for pesticidal effects such as by spraying on a leaf. Indirect methods of applications are not taught or contemplated in the specification.

Yates et al (1990)[1] describes an experiment undertaken to determine the toxicity of tall fescue extracts where the tall fescue was infected with *Acremonium coenophialum* endophyte. Yates does not teach or suggest applying the extract to another plant in order to transfer pesticidal properties. Yates also does not attribute pesticidal properties to pyrrolizidine alkaloids.

[1] Yates et al., 'Assay of Tall Fescue Seed Extracts, Fractions and Alkaloids Using the Large Milkweed Bug', J. Agric. Food Chem. 37:354-357 (1989).

US 2004/0141955 teaches of a novel endophytic fungi termed 'Muscodor' which is used to confer pest resistance to plants by inoculation of Muscodor species into the plant. A further option is described being use of a stabilised Muscodor placed adjacent or near the plant to be protected and the volatile compounds produced by the Muscodor provide the pesticidal effect. No disclosure is made regarding pyrrolizidine compounds, extracts of these compounds, or introducing these compounds into a plant. Pesticidal properties are only attributed to the Muscodor endophyte.

Casabuono et al 1997 teaches that loline alkaloids of *Festuca argentine* were asymptomatic and non-toxic at dose ranges from 31.25 to 125.0 mg/kg based on studies where such alkaloids were isolated and administered to mice as a concentrated aqueous suspension. No teaching is made within the paper regarding use of the isolated loline alkaloids as a pesticide. Of interest though is that loline alkaloids, whilst having a pesticidal affect, do not appear to be particularly toxic which may be useful in horticultural applications of the present invention.

From the above discussion, it should be appreciated that it would be desirable to have a pesticidal composition that utilised pesticidal protection mechanisms present in nature but without the need for example, to inoculate the plant with an endophyte.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

Compositions and methods are now described relating to the inventors unexpected finding that natural pesticidal effects observed in grass and endophyte combinations may be transferred to other plants without need to inoculate endophytes into plants on which the benefits are to be conferred.

For the purposes of this specification, the term 'composition' refers to one or more compounds in a close association.

The term 'pesticidal' refers to a composition for deterring or destroying plant, fungal, or animal pests including insects.

According to one aspect of the present invention there is provided a pesticidal composition obtained from an aqueous extraction of a plant and endophyte combination, wherein the aqueous extract contains at least one pyrrolizidine alkaloid compound, wherein the pyrrollzidine compound is of Formula [I] being:

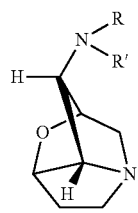

FORMULA [I]

wherein:
R=H or CH$_3$ and
R'=H, CH$_3$, CHO, COCH$_3$.

According to a further aspect of the present invention there is provided a plant with enhanced pest protection characterised in that the plant confers said pest protection upon application of a pesticidal composition wherein the pesticidal composition includes at least one pyrrolizidine alkaloid compound of Formula [I]:

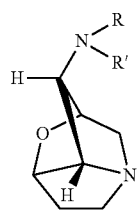

FORMULA [I]

wherein:
R=H or CH$_3$ and
R'=H, CH$_3$, CHO, COCH$_3$;
and further characterised in that the plant is not infected with an endophyte.

According to a further aspect of the present invention there is provided a method of producing a pesticidal composition by the steps of:
(a) cultivating at least one plant or part thereof inoculated with at least one endophyte and,
(b) extracting by way of aqueous extraction processes at least one pyrrolizidine alkaloid compound from the plant or part thereof to produce the pesticidal composition.

According to a further aspect of the present invention there is provided a method of conferring pest resistance to at least one plant by the steps of:
(a) producing a pesticidal composition from a natural source containing at least one pyrrolizidine alkaloid compound; and,
(b) applying the pesticidal composition to the medium in which the plant is growing allowing the plant to absorb the composition via the plants roots.

According to a further aspect of the present invention there is provided a method of conferring pest protection to at least one plant by the steps of:
(a) producing a pesticidal composition from a non-synthetic source containing at least one pyrrollzidine alkaloid compound; and,
(b) applying the pesticidal composition to a plant on which increased pest protection is to be conferred.

According to a further aspect of the present invention there is provided a method of conferring pest protection to at least one plant by the steps of:
(a) cultivating at least one plant or part thereof inoculated with at least one endophyte;
(b) extracting at least one pyrrolizidine alkaloid compound from the plant or part thereof to form a pesticidal composition and;
(a) applying the composition to a plant on which increased pest protection is to be conferred.

According to a further aspect of the present invention there is provided the use of a pesticidal composition in conferring pest resistance to at least one plant wherein the composition contains at least one pyrrolizidine alkaloid compound derived from a plant and endophyte combination with the structure of Formula [I] being:

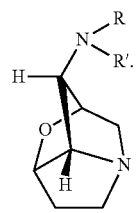

FORMULA [1]

wherein:
R=H or CH$_3$ and
R'=H, CH$_3$, CHO, COCH$_3$.

According to a further aspect of the present invention there is provided the use of a plant inoculated with an endophyte to produce a pesticidal composition containing at least one pesticidally effective pyrrolizidine alkaloid compound.

According to a further aspect of the present invention there is provided the use of an endophyte producing at least one pyrrolizidine alkaloid compound when in combination with a grass cultivar, to confer pest resistance to a plant that is not infected with an endophyte.

In one embodiment, the pesticidal composition includes at least one pyrrolizidine alkaloid compound produced from an endophyte and grass combination.

Preferably, the pyrrolizidine alkaloid compound or compounds is a 1-aminopyrrolizidine compound. More preferably, the pyrrolizidine alkaloid compound or compounds are as per the structure of Formula [I] being:

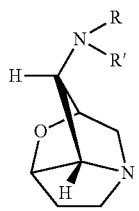

FORMULA [I]

wherein:
R=H or $CH_3$ and
R'=H, $CH_3$, CHO, $COCH_3$.

More specifically, Formula [I] includes:
loline where R=CH3 and R'=H;
norloline where R=H and R'=H;
N-methylloline where R=CH3 and R'=CH3;
N-formylloline where R=CH3 and R'=CHO;
N-formylnorioline where R=H and R'=CHO;
N-acetylloline where R=CH3 and =COCH3;
N-acetylnorioline where R=H and R'=COCH3.

Preferably, the plant or part thereof is derived from the genus *Festuca*. More preferably, the plant or part thereof is a meadow fescue or tall fescue species grass. For the purposes of this specification, reference will now be made to the plant or part thereof being derived from a grass plant. This should not be seen as limiting as it should be appreciated that other plants also are inoculated by endophytes which produce alkaloid compounds.

The term 'plant or part thereof' as used herein refers to the entire plant or seeds, roots, leaves, flowers, stems, pseudostems and the like. In the present invention, seeds have been found to be the most preferable source for extracting pyrrolizidine alkaloid compounds although, other plant parts (or the whole plant) may be used. It should be appreciated that the plant part used may be dependent on where the greatest levels of pyrrolizidine alkaloid compounds are produced and also dependent on extraction techniques used.

As may also be appreciated, the part of the plant used may also vary seasonally as well as for example, total alkaloid levels per plant increase in spring, reaches a peak at seed maturation, drops quickly with seed dispersal and stalk senescence and increases again during vegetative growth in late summer.

Preferably, the endophyte used is characterised by producing at least one pyrrolizidine alkaloid compound. More preferably, endophytes include those of the genera *Epiohloe* or *Neotyphodium*.

As noted above, the base grass plant is infected with endophytic fungi. Such combinations are well known in the art where the endophyte provides a symbiotic relationship with the grass and provides pest resistance to the infected grass.

Preferably, the plant to which the pesticidal composition is applied develops resistance to pests akin to that observed for a grass and endophyte combination but the plant does not include the endophyte. As may be appreciated, inoculation with an endophyte is a specialised process and a process that does not work for all plant species. Inoculation, if successful may also result in different properties, not necessarily pesticidal related. The pesticidal advantages of the endophyte are very useful hence the composition and method of the present invention allows transfer of the beneficial properties of the endophyte without the need to go through an inoculation process.

In one embodiment the resistance produced in the plant is systemic with the pesticidal composition being absorbed and circulated by the plant or organisms in the plant so as to confer a pest resistance to the plant.

In alternative embodiments the pesticide is a contact pesticide which deters pests via volatile production or, on contact with the pest, kills or deters the pest from eating the plant.

An example of this pest resistance mechanism includes direct deterring of pests feeding on the plant via volatile production and/or by a post digestive feedback mechanism where the pest eats a portion of the plant, ingests toxins and develops a learned response to not eat that plant again. It is likely that many interactions may occur to cause the observed resistance and the above example is provided by way of explanation and should not be seen as limiting.

Preferably the plant has resistance to both plant shoot feeding and root sucking and chewing pests. This feature of the present invention is particularly advantageous as it provides a full spectrum pesticide avoiding the need to use two or more pesticides in order to gain the desired effects.

More specifically, pest resistance may be developed to at least: grass grub (*Cotelydra zealandica*), porina larvae (*Wiseana* spp), milkweed bug (*Oncopeitus fasciatus*), aphid spp (*Rhopalosiphum padi* and *Schizaphis graminum*), Japanese beetle, spittle bug and diamond back moth. As should be obvious to persons skilled in the art, other insects known to be controlled by endophyte and plant associations are also candidates for pest protection according to the invention. The above list is provided by way of example only and should not be seen as limiting.

In one embodiment, a pesticidal composition is produced as an aqueous extract by the steps of grinding and mixing using seeds and water. As should be appreciated, seed grinding may occur before addition of water and mixing or may occur simultaneously with grinding occurring in conjunction with mixing with water. An aim of the extraction step is to release the pyrrollzidine alkaloid compounds from the seed. Many other methods are envisaged such as use of other solvents including alcohol in the extraction or other extraction techniques such as super critical fluid extraction, pressing, filtration methods and the like. However, water is a simple, inexpensive and environmentally friendly solvent. Also, water is useful in this instance as the pyrrolizidine alkaloid compounds of interest are sufficiently water soluble to produce useful amounts of these compounds in the resulting liquid to form an extract or pesticidal composition. The use of water extraction should not be seen as limiting as it should be appreciated that many separation techniques exist in the art which may be applicable to the present invention.

Preferably, the composition contains a pesticidally effective amount of at least one pyrrolizidine alkaloid to induce the desired response and is predetermined by routine testing. Where the ultimate response is insect resistance, an 'effective amount' or 'pesticidally effective amount' is defined to mean those quantities which will result in a significant resistance to a test group compared to an untreated group. The actual effective amount may vary with plant species and/or the target pest species stage of development, environmental conditions, nature of substrate, type of carrier, period of treatment and other related factors.

Based on trials completed by the inventor, a liquid extract pesticidal composition using water as the solvent and seeds as the plant part produces a solution containing effective amounts of pyrrolizidine alkaloids. For example, levels include a loline content of 311-1962 ppm, an N-acetylloline content of 36-354 ppm, an N-acetylnorloline content of 7-88 ppm and an N-formylloline content of 268-1520 ppm. Amounts are provided by way of illustration and the composition may include other alkaloids beyond those illustrated here. It should also be appreciated that alternative extraction methods may have greater extraction efficiency and thereby produce an extract composition containing greater (or lower) amounts of the above identified compounds. It should also be understood that other pyrrolizidine alkaloids present in the composition may also assist or influence the pesticidal effect.

Also, based on the inventor's experience, it is possible to dilute the concentration of the alkaloid content in the composition considerably and still have a beneficial effect. In a preferred embodiment, a lower threshold of a 12.5% by volume dilution may be made from a water based extraction of ground seed and which still includes sufficient levels of pyrrolizidine alkaloids to confer a pesticidal effect to plants on which the solution is applied. This result suggests that the pesticidal effect of the composition is strong and that only minimal amounts may be required in a final product therefore making the composition attractive and cost effective commercially.

As noted above, the pesticidal composition is applied to a plant or plants in order to confer pest resistance. Preferably, the delivery method or methods include pouring an aqueous solution of the composition onto the growing medium (e.g. soil, potting mix etc) surrounding the roots of the plant or plants and the solution is taken up into the plant by the plant roots. The mechanism for this is understood to be a leaching process of the composition into the soil and plant uptake via natural osmotic processes.

Alternative methods of delivery also include spraying a solution onto the plant; pouring a powder of the composition onto the plant directly or in the vicinity of the plant roots; soaking or immersion of a plant or part thereof in the composition; dusting the plant above the ground; fumigating the composition e.g. as an aerosol; insertion or placing a solid plug of composition into or adjacent the plant e.g. inserting the plug into a hole drilled into the plant stem or attaching the plug adjacent the plant stem; application as a prill or granule to the medium in which the plant grows; inserting the composition into a plant irrigation line; inserting the composition into a hydroponic system; and combinations thereof.

The above methods are provided by way of example only and it should be appreciated that other delivery methods may also be undertaken without departing from the scope of the invention. For further discussion, reference will be made to the composition being an aqueous solution watered onto the plant roots and absorbed into the plant via the plant roots. This should not be seen as limiting.

Plants to which pesticidal resistance may be conferred do not appear to be limited to any particular species or group of species. The inventor has found that pesticidal effects may be transferred to other grasses such as *Festuca* spp. and *Lolium* spp., brassicas including cabbage, cereal crops such as barley, horticultural crops such as tomato plants, and flowering crops such as roses. One surprising and useful result of the transfer in pest resistance is that the alkaloid compounds do not appear to transfer to edible portions of the plant such as the plant fruit. This may be advantageous in horticultural crops where it would be undesirable, at least from a marketing viewpoint, if the crop included alkaloid compounds that were ingested by humans.

From the above description it should be appreciate that the inventor has found that the pesticidal effects of endophytes in grass may be transferred to another plant without also having to transfer the endophyte. In effect, the symbiotic relationship between a grass and endophyte combination may be transferred to other plants without need to also inoculate the other plant with endophyte.

Uses of the pesticidal composition and method may include horticultural applications (e.g. market gardens, glasshouse crops and so on), viticulture (e.g. to prevent pests in wine producing grapes and grape plants), agriculture (e.g. to prevent pest predation of forage crops, cereal crops and so on). Addition of the alkaloid compound to drip irrigation or hydroponic systems is also a further usage options.

A further advantage of the present pesticidal composition and method is that they present an alternative 'natural' and renewable remedy against pests in plants contrary to existing methods of pest control such as using chemical based sprays such as Shield™ for control of pests in roses.

BRIEF DESCRIPTION OF DRAWINGS

Further aspects of the present invention will become apparent from the following description which is given by way of example only and with reference to the accompanying drawings in which:

FIG. 1 shows a graph comparing aphid numbers on plants after 21 days with and without treatment using a pesticidal composition in a cafeteria situation (Pots were randomised in 5 replicates);

FIG. 2 shows a graph comparing aphid numbers on plants after 27 days with and without treatment using a pesticidal composition in a cafeteria situation (As in FIG. 1);

FIG. 3 shows a graph comparing aphid numbers on nil endophyte fescue and ryegrass plants after 31 days with and without treatment using a pesticidal composition in a cafeteria situation (As in FIG. 1 aphids were counted when plants were destructively harvested);

FIG. 4 shows a graph comparing insect numbers on barley plants over time with and without treatment using a pesticidal composition in a cafeteria situation (insects were placed in an enclosure and were free to choose plants);

FIG. 5 shows a graph for varying strength solutions of pesticidal composition and the effect they had on mature aphid populations over time;

FIG. 6 shows a graph scoring relative plant health over time for plants infected with mature aphid populations and treated with varying strength solutions;

FIG. 7 shows a graph for varying strength solutions of pesticidal composition and the effect they had on immature aphid populations over time; and, FIG. 8 shows a graph scoring relative plant health over time for plants infected with immature aphid populations and treated with varying strength solutions.

BEST MODES FOR CARRYING OUT THE INVENTION

The invention is now described with reference to a series of experiments completed by the inventor, Experiments (presented as Examples below) were undertaken to determine several aspects being:

1. Can a pesticidal composition be produced from a plant/endophyte combination?
2. Can the pesticidal composition containing loline compounds be absorbed through their roots into grass plants that do not include an endophyte?
3. Do the pesticidal properties transfer to the plant?
4. Does the composition and method confer pest resistance to other insects?
5. Will treated plants have an effect as a pesticide in a choice cafeteria situation?
6. Does the pesticidal composition transfer to edible parts of the plant and therefore Influence whether or not the food produced from the plant contains loline compounds?

Example 1

Seed produced from a Meadow Fescue grass and endophyte combination was collected, ground and then mixed with water. The mixture was then further ground/macerated using a vigorous stirring method that both mixes and further breaks apart the seed fractions, After thorough mixing, the resulting solution was allowed to settle with seed husks and other solids separating out to the bottom of the mixing vessel. The liquid at the top of the vessel was collected, filtered and analysed to determine that a pesticidal composition was produced and what quantities of selected compounds were extracted. The process was repeated five times. A sixth sample was also obtained and analysed from the husks and residue of Grinding Number 4. This material was found to still contain high concentrations of loline compounds. Further improvements to extraction techniques are considered obvious and this method is provided by way of example only.

Results found in terms of various loline compounds measured are shown below in Table 1.

TABLE 1

Pesticidal Composition Contents

| Grinding Number | Pyrrolizidine Alkaloid Content [mg/kg or ppm] Total of NAL, NANL and NFL | NAL[1] | NANL[2] | NFL[3] |
|---|---|---|---|---|
| 1 | 311 | 36 | 7 | 268 |
| 2 | 464 | 75 | 30 | 359 |
| 3 | 444 | 70 | 27 | 347 |
| 4 | 597 | 90 | 40 | 467 |
| 5 | 423 | 63 | 16 | 344 |
| Residue from Grinding Number 4 | 1962 | 354 | 88 | 1520 |

[1] NAL refers to N-acetylloline
[2] NANL refers to N-acetylnorloline
[3] NFL refers to N-formylloline The above Example showed that a pesticidal composition can be produced from a plant/endophyte seed containing pyrrolizidine alkaloid compounds. The results for the extracted residue suggest that further extraction methods may be possible to extract more pyrrolizidine alkaloids.

Example 2

Pesticidal composition from Grinding Number 1 of Example 1 was watered onto the roots of endophyte free Fescue and Ryegrass plants grown in a glasshouse under controlled conditions into silica sand filled pots. Control plants were included in the plant samples and were watered with nil endophyte ground extract containing no pesticidal composition. Trial plants were each watered with 100 ml of each composition every second day with nutrient watered on alternate days. After 21 days, a sub-sample of leaf material was analysed to determine the uptake of pesticidal composition into the plants tested.

The results shown below in Table 2 for endophyte free Fescue plants and Table 3 for endophyte free Ryegrass plants clearly indicate transfer of the measured pyrrolizidine alkaloid compounds from the composition and into the plants via their root system

TABLE 2

Alkaloids in Endophyte Free Fescue Plants

| Plant Number | Pyrrolizidine Alkaloid Content [mg/kg or ppm] Total of NAL, NANL and NFL | NAL[1] | NANL[2] | NFL[3] |
|---|---|---|---|---|
| 1 | 767 | 119 | 0 | 648 |
| 2 | 548 | 69 | 0 | 479 |
| 3 | 577 | 95 | 0 | 482 |
| 4 | 461 | 56 | 0 | 405 |
| 5 | 420 | 38 | 0 | 382 |
| Average | 555 | 75 | 0 | 479 |

TABLE 3

Alkaloids in Endophyte Free Ryegrass Plants

| Plant Number | Pyrrolizidine Alkaloid Content [mg/kg or ppm] Total of NAL, NANL and NFL | NAL[1] | NANL[2] | NFL[3] |
|---|---|---|---|---|
| 1 | 1366 | 214 | 0 | 1152 |
| 2 | 828 | 87 | 44 | 697 |
| 3 | 790 | 84 | 27 | 680 |
| 4 | 392 | 40 | 0 | 352 |
| 5 | 376 | 37 | 0 | 340 |
| Average | 750 | 92 | 14 | 644 |

[1] NAL refers to N-acetylloline
[2] NANL refers to N-acetylnorloline
[3] NFL refers to N-formylloline

Example 3

To test whether or not pest protection transferred to the endophyte free plants, the plants used in Example 2 were subjected to aphid attack. Due to there being both treated and untreated (control) plants present in the same area and under the same growing conditions, the aphids were presented with a cafeteria situation where they were able to choose plants to feed on at will and without other factors influencing, The number of aphids on each plant was measured after 21 days, 27 days and 31 days post starting the trial with aphids being removed after each sampling date.

FIGS. 1 to 3 show the results of this trial. As can be seen on the graphs, aphid numbers were dramatically lower on treated plants as opposed to untreated plants showing a significant pesticidal effect from application of the pesticidal composition. Therefore it is clear that the pesticidal composition does have a pesticidal effect.

Example 4

A further trial was completed to determine if the pesticidal effect extends to root feeding insects such as grass grub.

Small samples of carrot were produced and soaked in pesticidal composition from Grinding Number 2 in Example 1. Additional control treatment samples were also tested being fresh carrot, carrot soaked in water, and carrot soaked in nil endophyte extract. Grass grubs were fed the various samples in a no-choice arrangement and after 3 days, the amount of carrot eaten was observed and measured.

Observations noted were that carrot soaked with pesticidal composition was either not eaten or only slightly eaten. In contrast, control samples were completely eaten. Comparative measurements of the grass grubs tested showed that grubs fed treated carrot showed a weight loss compared to control samples and some grub mortality for treated samples not observed in control samples.

The above trial confirms that the pesticidal composition has pesticidal effects, on root feeding pests including grass grub. Grass grub exposed to the pesticidal material; refused at subsequent feeding to consume fresh untreated carrots; suggesting a post digestive feedback response.

Example 5

A further trial was completed to determine if the pesticidal effect could be transferred to plants other than those of the Graminae family.

Cabbage *brassica* were tested with the pesticidal composition of Grind Number 3 of Example 1 watered onto the pots in which the trial cabbage plants were grown in silica sand.

The results found are shown in Table 3 below.

TABLE 3

| Cabbage Treated with Pesticidal Composition Pyrrolizidine Alkaloid Content [mg/kg or ppm] | | | |
|---|---|---|---|
| Total of NAL, NANL and NFL | NAL[1] | NANL[2] | NFL[1] |
| 154 | 6 | 0 | 148 |

[1]NAL refers to N-acetylloline
[2]NANL refers to N-acetylnorloline

[1] NAL refers to N-acetylloline
[2] NANL refers to N-acetylnorloline
[1] NFL refers to N-formylloline The results found show that transfer occurs into plants other than just grasses.

Example 6

A further experiment was completed to confirm that the pesticidal effect could be transferred to further plants. The trial used barley plants treated with the pesticidal composition of Grinding Number 5 of Example 1 alongside control samples which were untreated. The plants were also subjected to insect attack in order to explicitly show the pesticidal effect and to determine if the insects responded in a cafeteria situation as expected.

Figure 4:
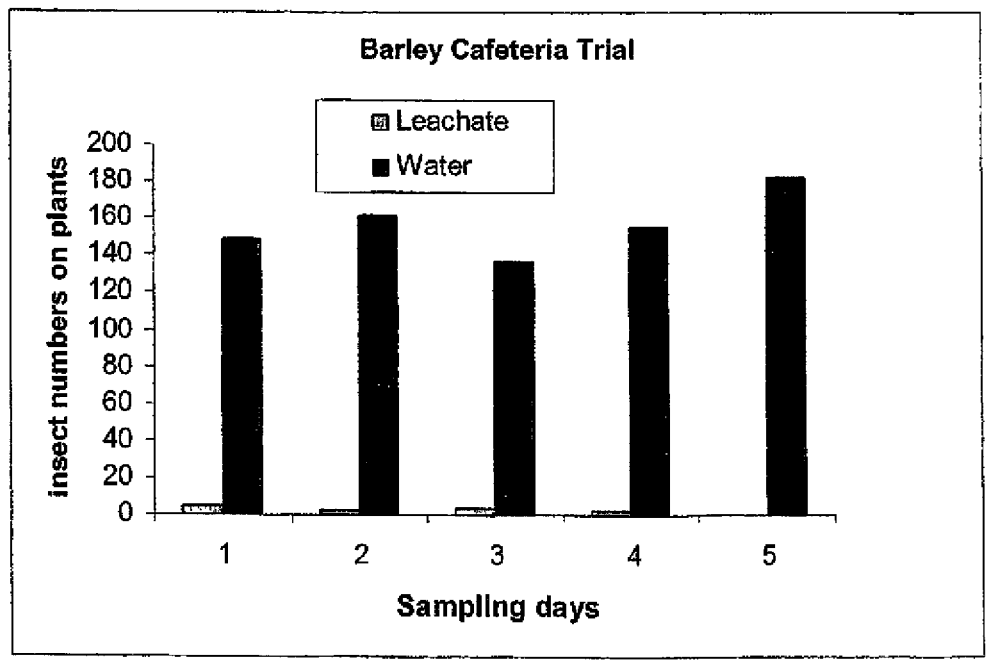

As shown in FIG. 4, the pesticidal effect was clearly apparent with insect numbers dramatically different between treated and untreated barley samples. The trial also shows again that the effect may be transferred to plants other than grasses.

Example 7

Barley plants were further tested to determine the concentration at which the pesticidal composition could be diluted and still achieve pesticidal results Barley plants were placed in inert material and the plant samples were treated with varying concentrations of pesticidal composition produced from Grinding Number 5 of Example 1. Concentrations were from 100% being the composition of Grinding Number 5 and diluted using water to concentrations of 50%, 25%, 12.5%, and 6%. A control was also used with no treatment composition. A total of 10 aphids were placed on each plant after treatment (or no treatment for the control) described above.

The effect was tested using both mature and immature aphids (Bird Cherry Oat Aphids (*R. padi*) with ten insects placed on each plant on day 1 of the trial. Mature insects would be expected to multiply quickly placing more stress on the plant whereas immature insects would be expected to have a lag effect before multiplying.

Figure 5:
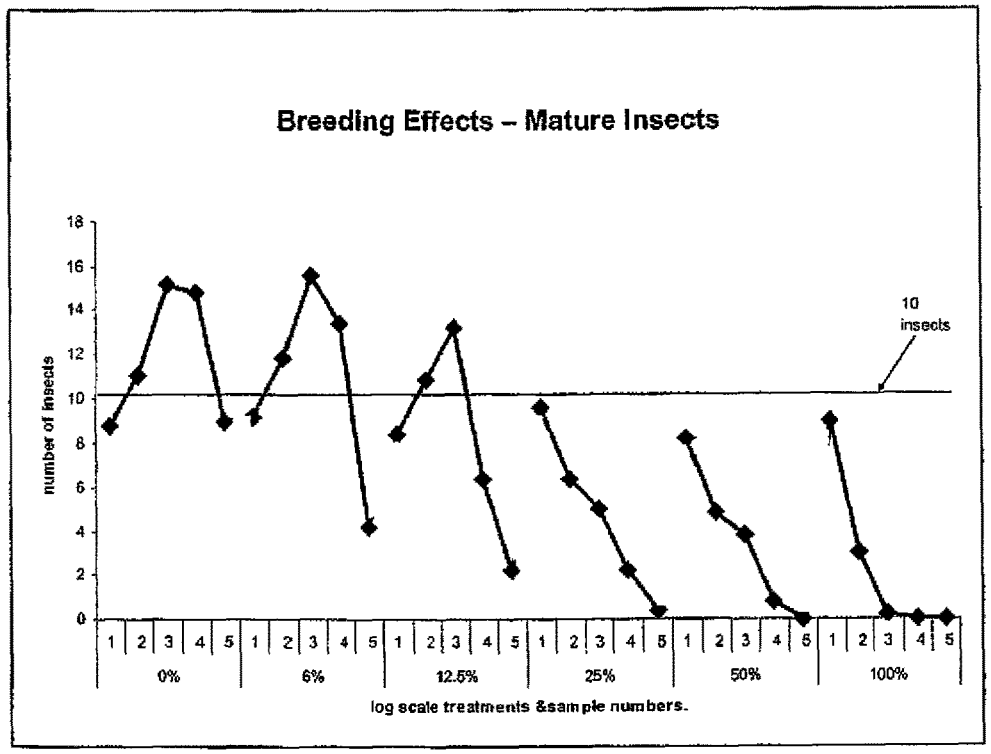
Figure 7:
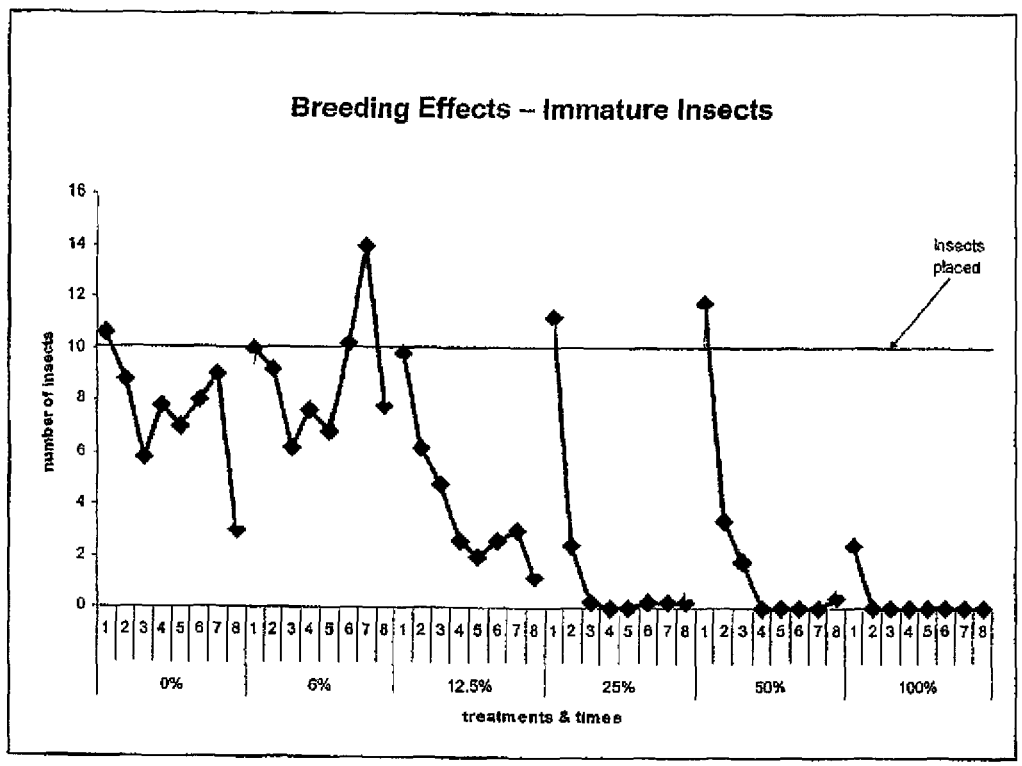

As can be seen in FIG. 5, mature insects multiplied as expected for concentrations lower than 25% but for concentrations of 12.5% or greater the multiplication was reduced or completely stopped. FIG. 7 shows the effect for immature insects which was even more marked with a 12.5% concentration being sufficient to halt insect multiplication.

Figure 6:
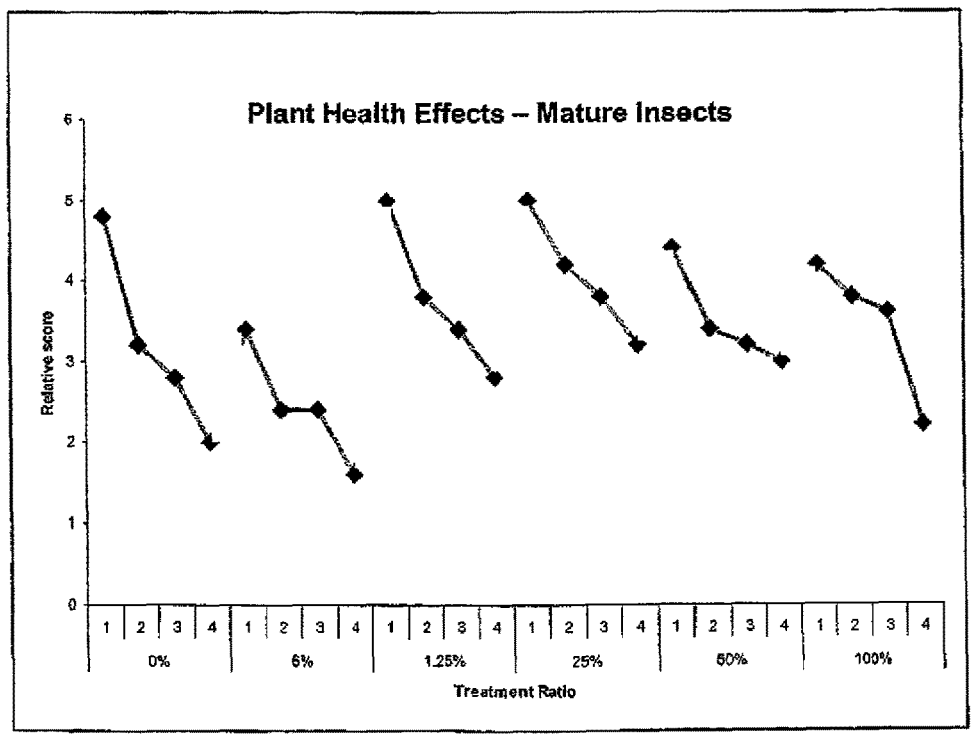
Figure 8:
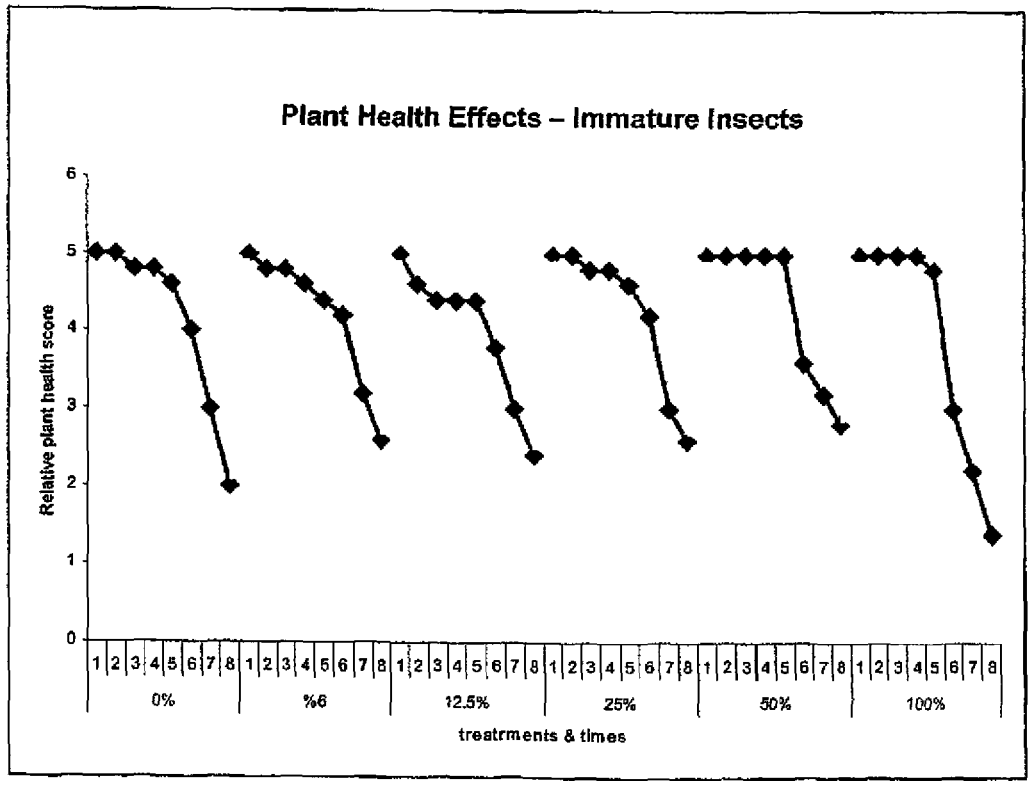

FIGS. 6 and 8 show observations of the plant health over time once the plants were subjected to insect attack. In FIG. 6, plant health decreases rapidly for low concentration treatments. In FIG. 8 the effect is more noticeable with plants remaining healthy for longer as the concentration of treatment increased. It should be noted in both cases that one would expect a drop in plant health owing to the plant naturally depleting the nutrient supply and being subjected to incessant insect attack.

The above trial shows that the pesticidal effect is strong with a dilution to 12.5% by volume still providing pesticidal effects. With improved extraction techniques, it should be appreciated that the composition is likely to be cost effective due to only low dilutions required to achieve the desired result.

Example 8

A further trial was completed to determine if the pesticidal effect could be transferred to tomato (*Solanum lycopersicum*) plants and also to determine if the pyrrolizidine alkaloids transfer into the fruit and/or leaves of the plant.

30 tomato plants were grown under controlled conditions and either treated with the solution of Grinding Number 4 of Example 1 or left untreated (control).

Once the plants had grown to a stage where multiple green fruit had appeared and were maturing, samples were taken to determine the loline compound levels. Loline compounds were detected in tomato plant stems (15 to 25 ppm) but no loline compounds were detected in the leaves or plant fruit.

The trial shows that it is unlikely that pesticidal composition used in the present invention will carry through into the human food chain by transfer of pesticidal compounds into leaves of fruit produced by the plant used for edible products.

Example 9

A further trial was completed using the seed residue from Grinding Number 4 of Example 1. As noted in Example 1, the pesticidal compounds measured in the residue were still considerable.

The residue was placed around the roots of rose plants in the environment that had not previously been treated for pests and observations made on a regular basis to look for any visual signs of insect attack.

In the time period observed (over 20 days), no observations were made of insect attack and the roses remained free of pests such as aphids. Given the amount of chemical sprays used on roses to control pests, the qualitative results found in this Example are at least promising as an alternative pest treatment method.

Example 10

Other delivery methods are described.

In one example, the pesticidal compositions produced in Example 1 are dried and formed into a powder. The powder is then spread around the roots of the plant and watered into the ground. Alternatively, the powder may be compressed into a solid plug and inserted into or adjacent the plant stem and released into the plant by normal plant osmotic action.

The powder or a liquid may also be formulated so as to release the pesticidal composition in a slow or fast manner as used in many fertiliser applications. As an example, one type of slow release fertiliser is a product named Osmocote™ which may be a granular product that releases fertiliser in a slow manner. The pesticidal composition of the present invention may be added to the Osmocote™ to produce a dual purpose product both feeding a plant and protecting it from pests.

A further option is to spray a liquid solution containing the pesticidal composition onto the plant or dust the plant with a powdered pesticidal composition. A yet further option is an aerosol containing pesticidal composition or the addition of the pesticidal compounds to hydroponic or drip irrigation systems.

It should be appreciated form the above Examples that there is provided a pesticidal composition containing naturally occurring compounds. The composition has been shown to be useful in transferring the pesticidal effects normally attributed to endophyte infection from an endophyte and plant combination into a plant that does not have an endophyte. The result is that pest resistance is conferred to the plant without need for inoculation.

Aspects of the present invention have been described by way of example only and it should be appreciated that modifications and additions may be made thereto without departing from the scope thereof as defined in the appended claims.

What we claim is:

1. A method of producing an insecticidal composition with systemic properties on application to a plant consisting of:

(a) cultivating at least one *Festuca* species grass plant or part thereof inoculated with at least one endophyte; and (b) extracting at least one pyrrolizidine alkaloid compound from the at least one *Festuca* species grass plant or part thereof in (a) using water only to produce the insecticidal composition comprising the at least one pyrrolizidine alkaloid compound and the water.

2. The method of claim 1, wherein the at least one pyrrolizidine alkaloid compound is a 1-aminopyrrolizidine compound.

3. The method of claim 1, wherein the at least one *Festuca* species grass plant or part thereof in step (b) is selected from: the entire plant, seeds, roots, leaves, flowers, stems, pseudo-stems.

4. The method of claim 1, wherein the endophyte used is of the genus *Epichloe* or *Neotyphodium*.

5. The method of claim 1, wherein the plant to which the insecticidal composition is applied does not include an endophyte.

6. The method of claim 1, wherein the plants to which the insecticidal composition is applied are selected from the group consisting of: grasses, brassicas, cereal crops, horticultural crops, and flowering crops.

7. The method of claim 1, wherein the at least one pyrrolizidine alkaloid compound is a 1-aminopyrrolizidine compound having the structure of Formula I:

FORMULA I 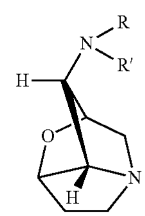 wherein:

R=H or $CH_3$ and

R'=H, $CH_3$, CHO, $COCH_3$.

8. The method of claim 6, wherein the plants to which the pesticidal composition is applied are selected from the group consisting of *Festuca* spp., *Lolium* spp., cabbage, barley, tomato plants and roses.

* * * * *